United States Patent [19]

Peery et al.

[11] Patent Number: 5,773,214
[45] Date of Patent: Jun. 30, 1998

US005773214A

[54] **MULTIPLE DRUG RESISTANCE GENE OF *ASPERGILLUS FLAVUS***

[75] Inventors: Robert B. Peery, Brownsburg; Paul L. Skatrud, Greenwood, both of Ind.

[73] Assignee: Eli Lilly and Company, Indianapolis, Ind.

[21] Appl. No.: 395,246

[22] Filed: Feb. 27, 1995

[51] Int. Cl.$^6$ .............................. C12Q 1/68; C12N 1/20; C12N 1/14; C12N 15/00
[52] U.S. Cl. ..................... 435/6; 435/252.3; 435/254.11; 435/254.2; 435/254.21; 435/320.1; 536/23.74; 536/25.32
[58] Field of Search ....................... 435/6, 252.3, 254.11, 435/320.1; 536/23.74, 25.32

[56] References Cited

U.S. PATENT DOCUMENTS

| 5,057,493 | 10/1991 | Takesako et al. | 514/11 |
|---|---|---|---|
| 5,158,876 | 10/1992 | Takesako et al. | 435/71.1 |
| 5,516,655 | 5/1996 | Peery et al. | 435/69.1 |

FOREIGN PATENT DOCUMENTS

92/11034   7/1992   WIPO.

OTHER PUBLICATIONS

Tiligada, E. et al., 1993, Br. J. Pharmacol. 108:233.
Gottesman, M. and Pastan, I., Feb. 1983, TIPS 91:54–58.
Fojo, A. et al., 1987, Proc. Natl. Acade. Sci. USA 84:265–269.
Gottesman, M. Pastan, I., 1993, Annu. Rev. Biochem. 62:385–427.
Pastan, I. and Gottesman, M., 1991, Annu. Rev. Med. 42:277–286.
Flier, J.S. and Underhill, L.H., 1987, New Eng. J. of Med. 316(22):1388–1393.
Gottesman, M. and Pastan, I., 1988, J. of Biol. Chem. 263(25):12163–12166.
Raymond, M. et al., 1994, Mol. and Cell. Biol. 14(1):277–286.
Ruetz, S. et al., 1993, Proc. Natl. Acad. Sci. USA 90:11588–11592.
Raymond, M. et al., 1992, Science 256:232–234.
Nishi K., et al., 1992, Molecular Microbiology 6(6), 761–769.

*Primary Examiner*—Robert A. Wax
*Assistant Examiner*—Lisa J. Hobbs
*Attorney, Agent, or Firm*—Thomas D. Webster; Thomas G. Plant; David E. Boone

[57] ABSTRACT

The invention provides isolated nucleic acid compounds encoding a multiple drug resistance protein of *Aspergillus flavus*. Vectors and transformed host cells comprising the multiple drug resistance-encoding DNA of *Aspergillus flavus* MDR-1 are also provided. The invention further provides assays which utilize these transformed host cells.

20 Claims, 2 Drawing Sheets

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 3924 base pairs
( B ) TYPE: nucleic acid (C) STRANDEDNESS: single
(D) TOPOLOGY: linear (ii) MOLECULE TYPE: cDNA (ix) FEATURE:
(A) NAME/KEY: CDS
(B) LOCATION: 1..3924

(xi) SEQUENCE DESCRIPTION: SEQ ID NO:1:

```
ATG  AAG  TCC  GAC  AAG  GAT  ATA  CTG  ATG  AAG  CCG  CTC  CCA  AAG  TCT  CCT       48
Met  Lys  Ser  Asp  Lys  Asp  Ile  Leu  Met  Lys  Pro  Leu  Pro  Lys  Ser  Pro
 1              5                        10                       15

GGG  ACG  GGC  AGT  ACG  ACT  ACG  GGT  CAC  TCT  GTC  TCG  CAC  GCT  GAA  GAG       96
Gly  Thr  Gly  Ser  Thr  Thr  Thr  Gly  His  Ser  Val  Ser  His  Ala  Glu  Glu
                 20                       25                       30

GTC  CTC  GAT  CGA  CAG  CTC  CAT  ACG  CCG  GTG  TCG  CAA  ATC  GGC  TTT  TTT      144
Val  Leu  Asp  Arg  Gln  Leu  His  Thr  Pro  Val  Ser  Gln  Ile  Gly  Phe  Phe
             35                       40                       45

GGT  ATC  TAT  CGA  TAT  GCG  ACT  CGA  TGG  GAT  GTC  GCC  ATT  CTC  TTC  GGC      192
Gly  Ile  Tyr  Arg  Tyr  Ala  Thr  Arg  Trp  Asp  Val  Ala  Ile  Leu  Phe  Gly
         50                       55                       60

AGT  GCG  CTT  GCT  GCG  ATC  GCA  GGC  GGT  GCA  GCA  CTA  CCT  CTC  TTC  ACG      240
Ser  Ala  Leu  Ala  Ala  Ile  Ala  Gly  Gly  Ala  Ala  Leu  Pro  Leu  Phe  Thr
 65                       70                       75                       80

GTC  CTC  TTC  GGC  AGG  TTG  ACG  TCG  ACC  TTT  CAA  GAC  ATC  GCT  ACC  CAT      288
Val  Leu  Phe  Gly  Arg  Leu  Thr  Ser  Thr  Phe  Gln  Asp  Ile  Ala  Thr  His
                 85                       90                       95

CGG  ATT  ACT  TAC  GAT  CAC  TTC  CAT  CAC  GAG  CTG  ACC  AAG  AAT  GTG  GTC      336
Arg  Ile  Thr  Tyr  Asp  His  Phe  His  His  Glu  Leu  Thr  Lys  Asn  Val  Val
            100                      105                      110

TAC  TTC  ATA  TAC  TTG  GGT  GCT  GCT  GAG  TTC  GTC  GCG  ATT  TAT  CTA  GCG      384
Tyr  Phe  Ile  Tyr  Leu  Gly  Ala  Ala  Glu  Phe  Val  Ala  Ile  Tyr  Leu  Ala
        115                      120                      125

ACC  GTC  GGC  TTC  ATT  TAT  ACC  GGC  GAC  CAT  GTC  GTA  CAG  CAG  ATT  CGG      432
Thr  Val  Gly  Phe  Ile  Tyr  Thr  Gly  Asp  His  Val  Val  Gln  Gln  Ile  Arg
    130                      135                      140

GTG  GAA  TAC  TTC  CAG  GCT  ATC  TTA  AGG  CAG  AAT  ATT  GCC  TTC  TTC  GAC      480
Val  Glu  Tyr  Phe  Gln  Ala  Ile  Leu  Arg  Gln  Asn  Ile  Ala  Phe  Phe  Asp
145                      150                      155                      160

ACT  CTT  GGT  GCT  GGG  GAG  ATC  ACA  ACG  AGG  ATC  ACC  GCC  GAC  ACG  AAC      528
Thr  Leu  Gly  Ala  Gly  Glu  Ile  Thr  Thr  Arg  Ile  Thr  Ala  Asp  Thr  Asn
                 165                      170                      175

CTG  ATT  CAA  GAC  GGT  ATC  TCC  GAA  AAG  GTC  GGC  CTA  GCC  TTG  ACC  GGG      576
Leu  Ile  Gln  Asp  Gly  Ile  Ser  Glu  Lys  Val  Gly  Leu  Ala  Leu  Thr  Gly
             180                      185                      190

CTT  TCG  ACG  TTC  GTG  ACG  GCG  TTC  ATC  ATC  GCC  TAT  ATA  AAG  AAC  TGG      624
Leu  Ser  Thr  Phe  Val  Thr  Ala  Phe  Ile  Ile  Ala  Tyr  Ile  Lys  Asn  Trp
        195                      200                      205

AAG  CTG  GCA  CTA  ATC  TGT  AGT  GCC  AGC  CTG  CTC  GCA  TTG  CTG  TTG  ACC      672
Lys  Leu  Ala  Leu  Ile  Cys  Ser  Ala  Ser  Leu  Leu  Ala  Leu  Leu  Leu  Thr
    210                      215                      220

ATG  GGT  GGT  TGC  TCC  ACC  CTC  ATG  CTC  ATT  TTT  AGC  AAG  AAA  GCA  TTG      720
Met  Gly  Gly  Cys  Ser  Thr  Leu  Met  Leu  Ile  Phe  Ser  Lys  Lys  Ala  Leu
225                      230                      235                      240

GAA  TAC  CAG  GGT  CGT  GGC  GCC  AGT  ATG  GCC  GAG  GAC  ATC  CTT  GAC  TCC      768
Glu  Tyr  Gln  Gly  Arg  Gly  Ala  Ser  Met  Ala  Glu  Asp  Ile  Leu  Asp  Ser
                 245                      250                      255

ATC  CGG  ACC  GTC  GCA  GCG  TTT  AAT  GCT  CAG  GAA  ACA  CTG  GCG  CGG  AAG      816
Ile  Arg  Thr  Val  Ala  Ala  Phe  Asn  Ala  Gln  Glu  Thr  Leu  Ala  Arg  Lys
             260                      265                      270

TAC  GAA  TCG  CAT  CTC  AAG  GAT  GCC  GAA  GGA  CCC  GGA  ATG  AAG  TCA  AAA      864
```

|  |  |  |  |  |  |  |  |  |  |  |  |  |  |  |  |  |
|---|---|---|---|---|---|---|---|---|---|---|---|---|---|---|---|---|
| Tyr | Glu | Ser | His | Leu | Lys | Asp | Ala | Glu | Gly | Pro | Gly | Met | Lys | Ser | Lys | |
|  |  | 275 |  |  |  | 280 |  |  |  | 285 |  |  |  |  |  | |
| GTG | ATC | TTC | GCC | ATC | ATG | GTG | GGA | GCA | TTA | CTA | TGC | ATC | ATG | TAT | CTC | 912 |
| Val | Ile | Phe | Ala | Ile | Met | Val | Gly | Ala | Leu | Leu | Cys | Ile | Met | Tyr | Leu | |
|  | 290 |  |  |  | 295 |  |  |  |  | 300 |  |  |  |  |  | |
| AAC | TAT | GGA | CTT | GGC | TTC | TGG | ATG | GGG | TCT | CGC | TTC | CTC | GTC | GAA | GGA | 960 |
| Asn | Tyr | Gly | Leu | Gly | Phe | Trp | Met | Gly | Ser | Arg | Phe | Leu | Val | Glu | Gly | |
| 305 |  |  |  |  | 310 |  |  |  |  | 315 |  |  |  |  | 320 | |
| ATC | AGT | AAC | ATC | AAA | GCC | GGG | GAT | GTG | CTG | ACC | ATC | ATG | ATG | GCC | ATC | 1008 |
| Ile | Ser | Asn | Ile | Lys | Ala | Gly | Asp | Val | Leu | Thr | Ile | Met | Met | Ala | Ile | |
|  |  |  |  | 325 |  |  |  |  | 330 |  |  |  |  | 335 |  | |
| ATC | CTA | GGT | TCC | TAT | AAT | CTG | GGC | AAT | GTG | GCC | CCC | AAT | GGA | CAA | GCG | 1056 |
| Ile | Leu | Gly | Ser | Tyr | Asn | Leu | Gly | Asn | Val | Ala | Pro | Asn | Gly | Gln | Ala | |
|  |  |  | 340 |  |  |  |  | 345 |  |  |  |  | 350 |  |  | |
| CTG | TCG | GAC | GCT | GTG | GCG | GCA | GCA | TCA | AAG | CTG | TAT | GGC | ACC | ATT | GAC | 1104 |
| Leu | Ser | Asp | Ala | Val | Ala | Ala | Ala | Ser | Lys | Leu | Tyr | Gly | Thr | Ile | Asp | |
|  |  | 355 |  |  |  |  | 360 |  |  |  |  | 365 |  |  |  | |
| CGT | CAA | TCC | CCT | TTA | GAT | GCG | TTG | TCC | GAT | CAG | GGC | AAG | ACG | CTG | GAG | 1152 |
| Arg | Gln | Ser | Pro | Leu | Asp | Ala | Leu | Ser | Asp | Gln | Gly | Lys | Thr | Leu | Glu | |
| 370 |  |  |  |  | 375 |  |  |  |  | 380 |  |  |  |  |  | |
| TTT | GTC | CGA | GGA | AAT | ATT | GTA | CTC | CAG | AAC | ATC | AGG | CAC | GTT | TAT | CCC | 1200 |
| Phe | Val | Arg | Gly | Asn | Ile | Val | Leu | Gln | Asn | Ile | Arg | His | Val | Tyr | Pro | |
| 385 |  |  |  | 390 |  |  |  |  | 395 |  |  |  |  |  | 400 | |
| TCG | CGA | CCC | GAG | GTC | ACT | GTT | GCC | CAT | GAT | CTG | AGT | TGC | TAT | ATT | CCT | 1248 |
| Ser | Arg | Pro | Glu | Val | Thr | Val | Ala | His | Asp | Leu | Ser | Cys | Tyr | Ile | Pro | |
|  |  |  |  | 405 |  |  |  |  | 410 |  |  |  |  | 415 |  | |
| GCC | GGT | AAG | ACG | ACT | GCC | TTC | GTG | GGT | CCC | TCA | GGG | TCC | GGC | AAA | AGT | 1296 |
| Ala | Gly | Lys | Thr | Thr | Ala | Phe | Val | Gly | Pro | Ser | Gly | Ser | Gly | Lys | Ser | |
|  |  |  | 420 |  |  |  |  | 425 |  |  |  |  | 430 |  |  | |
| ACC | ATC | ATC | AGC | TTG | CTT | GAG | CGG | TTT | TAT | GAC | CCA | GTC | GCG | GGG | ACC | 1344 |
| Thr | Ile | Ile | Ser | Leu | Leu | Glu | Arg | Phe | Tyr | Asp | Pro | Val | Ala | Gly | Thr | |
|  |  | 435 |  |  |  |  | 440 |  |  |  |  | 445 |  |  |  | |
| ATT | ATG | CTC | GAC | GGC | CAC | GAT | ATC | CAG | ACA | TTG | AAT | CTC | CGA | TGG | CTG | 1392 |
| Ile | Met | Leu | Asp | Gly | His | Asp | Ile | Gln | Thr | Leu | Asn | Leu | Arg | Trp | Leu | |
|  | 450 |  |  |  |  | 455 |  |  |  |  | 460 |  |  |  |  | |
| CGA | CAG | CAA | ATG | TCG | CTC | GTG | TCG | CAA | GAG | CCG | AGA | CTC | TTC | GCC | ACC | 1440 |
| Arg | Gln | Gln | Met | Ser | Leu | Val | Ser | Gln | Glu | Pro | Arg | Leu | Phe | Ala | Thr | |
| 465 |  |  |  |  | 470 |  |  |  |  | 475 |  |  |  |  | 480 | |
| ACC | ATC | GCG | GAG | AAT | ATC | CGT | TAT | GGT | ATC | ATT | GGC | TCT | CGA | TTC | GAA | 1488 |
| Thr | Ile | Ala | Glu | Asn | Ile | Arg | Tyr | Gly | Ile | Ile | Gly | Ser | Arg | Phe | Glu | |
|  |  |  |  | 485 |  |  |  |  | 490 |  |  |  |  | 495 |  | |
| AAG | GAA | TCG | ACG | TAC | GAG | ATC | CGA | AAG | CGA | GTC | GAA | GCA | GCA | GCT | CGA | 1536 |
| Lys | Glu | Ser | Thr | Tyr | Glu | Ile | Arg | Lys | Arg | Val | Glu | Ala | Ala | Ala | Arg | |
|  |  |  | 500 |  |  |  |  | 505 |  |  |  |  | 510 |  |  | |
| ATG | GCA | AAT | GCG | CAC | GAC | TTC | ATC | ATG | GCG | CTT | CCG | AAT | GGT | TAT | GAT | 1584 |
| Met | Ala | Asn | Ala | His | Asp | Phe | Ile | Met | Ala | Leu | Pro | Asn | Gly | Tyr | Asp | |
|  |  | 515 |  |  |  |  | 520 |  |  |  |  | 525 |  |  |  | |
| ACA | AAT | ATC | GAG | AGC | TTC | TCG | CTT | TCT | GGG | GGC | CAG | AAG | CAG | CGC | ATC | 1632 |
| Thr | Asn | Ile | Glu | Ser | Phe | Ser | Leu | Ser | Gly | Gly | Gln | Lys | Gln | Arg | Ile | |
|  | 530 |  |  |  |  | 535 |  |  |  |  | 540 |  |  |  |  | |
| GCT | ATT | GCC | AGA | GCT | ATC | ATA | AAA | GAC | CCT | AAG | ATC | CTA | CTC | TTA | GAC | 1680 |
| Ala | Ile | Ala | Arg | Ala | Ile | Ile | Lys | Asp | Pro | Lys | Ile | Leu | Leu | Leu | Asp | |
| 545 |  |  |  |  | 550 |  |  |  |  | 555 |  |  |  |  | 560 | |
| GAA | GCA | ACA | TCC | GCC | TTG | GAC | ACG | AAA | TCC | GAA | AAG | CTC | GTT | CAG | GCA | 1728 |
| Glu | Ala | Thr | Ser | Ala | Leu | Asp | Thr | Lys | Ser | Glu | Lys | Leu | Val | Gln | Ala | |
|  |  |  |  | 565 |  |  |  |  | 570 |  |  |  |  | 575 |  | |
| GCG | CTT | GAC | AAG | GCT | TCT | AAG | GGT | AGA | ACG | ACT | ATT | GTC | ATC | GCT | CAT | 1776 |
| Ala | Leu | Asp | Lys | Ala | Ser | Lys | Gly | Arg | Thr | Thr | Ile | Val | Ile | Ala | His | |
|  |  |  | 580 |  |  |  |  | 585 |  |  |  |  | 590 |  |  | |
| CGG | CTG | TCC | ACA | ATC | CAG | AAG | GCA | TAC | AAC | ATC | ATT | GTT | CTT | GCC | AAT | 1824 |

| | | | | | | | | | | | | | | | | |
|---|---|---|---|---|---|---|---|---|---|---|---|---|---|---|---|---|
| Arg | Leu | Ser | Thr | Ile | Gln | Lys | Ala | Tyr | Asn | Ile | Ile | Val | Leu | Ala | Asn | |
| | | 595 | | | | 600 | | | | | 605 | | | | | |
| GGT | CAG | ATT | GTT | GAG | CAA | GGG | CCG | CAT | GAG | CAT | TTG | ATG | GAT | CGA | CGG | 1872 |
| Gly | Gln | Ile | Val | Glu | Gln | Gly | Pro | His | Glu | His | Leu | Met | Asp | Arg | Arg | |
| 610 | | | | | 615 | | | | | | 620 | | | | | |
| GGG | ATC | TAT | TGT | GAC | ATG | GTG | GAA | GCG | CAC | GAG | ATT | AAG | AAA | CGG | TAC | 1920 |
| Gly | Ile | Tyr | Cys | Asp | Met | Val | Glu | Ala | His | Glu | Ile | Lys | Lys | Arg | Tyr | |
| 625 | | | | | 630 | | | | | 635 | | | | | 640 | |
| TCG | AGA | TAC | TCC | AAG | AGA | TAT | TCC | CAG | CTA | TTG | ACG | AAC | TTG | TCC | CCT | 1968 |
| Ser | Arg | Tyr | Ser | Lys | Arg | Tyr | Ser | Gln | Leu | Leu | Thr | Asn | Leu | Ser | Pro | |
| | | | | 645 | | | | | 650 | | | | | 655 | | |
| AAG | CAT | AAC | CCA | ATG | ACC | TTC | TTC | TTC | GAC | AAA | GAT | TAC | CCG | GGC | GAT | 2016 |
| Lys | His | Asn | Pro | Met | Thr | Phe | Phe | Phe | Asp | Lys | Asp | Tyr | Pro | Gly | Asp | |
| | | | 660 | | | | | 665 | | | | | 670 | | | |
| GAC | GAG | TCC | GAT | ATT | TAC | AGC | ATC | CTC | AGT | GAT | GAC | GCA | TCC | GAT | ATT | 2064 |
| Asp | Glu | Ser | Asp | Ile | Tyr | Ser | Ile | Leu | Ser | Asp | Asp | Ala | Ser | Asp | Ile | |
| | | 675 | | | | | 680 | | | | | 685 | | | | |
| GGA | TTG | CAC | ACT | GGG | GAG | AAA | CAA | AGA | CCA | GTG | TCG | AGA | ATG | TCA | CTA | 2112 |
| Gly | Leu | His | Thr | Gly | Glu | Lys | Gln | Arg | Pro | Val | Ser | Arg | Met | Ser | Leu | |
| | 690 | | | | | 695 | | | | | 700 | | | | | |
| TCT | CAT | CTC | ATG | CAG | CCG | GTC | AAG | GAA | GAG | GCA | TAT | TCT | TTC | TGG | ACT | 2160 |
| Ser | His | Leu | Met | Gln | Pro | Val | Lys | Glu | Glu | Ala | Tyr | Ser | Phe | Trp | Thr | |
| 705 | | | | | 710 | | | | | 715 | | | | | 720 | |
| TTG | TTC | AAG | TTC | CTT | GCC | TCG | TTC | AAC | CGT | CCC | GAG | TGG | CCG | TTT | TTA | 2208 |
| Leu | Phe | Lys | Phe | Leu | Ala | Ser | Phe | Asn | Arg | Pro | Glu | Trp | Pro | Phe | Leu | |
| | | | | 725 | | | | | 730 | | | | | 735 | | |
| TTA | CTA | GGG | CTC | TGC | GCA | TCT | ATA | CTG | GCA | GGG | GGG | ATC | CAA | CCA | TCG | 2256 |
| Leu | Leu | Gly | Leu | Cys | Ala | Ser | Ile | Leu | Ala | Gly | Gly | Ile | Gln | Pro | Ser | |
| | | | 740 | | | | | 745 | | | | | 750 | | | |
| CAG | GCT | GTG | CTG | TTT | GCG | AAG | GCT | GTC | AGC | ACC | CTC | AGC | CTG | CCC | CCT | 2304 |
| Gln | Ala | Val | Leu | Phe | Ala | Lys | Ala | Val | Ser | Thr | Leu | Ser | Leu | Pro | Pro | |
| | | 755 | | | | | 760 | | | | | 765 | | | | |
| CTT | GAA | TAT | CCG | AAG | CTC | CGG | CAC | GAT | GCC | AAC | TTC | TGG | TGC | CTC | ATG | 2352 |
| Leu | Glu | Tyr | Pro | Lys | Leu | Arg | His | Asp | Ala | Asn | Phe | Trp | Cys | Leu | Met | |
| | 770 | | | | | 775 | | | | | 780 | | | | | |
| TTT | CTC | ATG | ATT | GGC | ATT | GTG | TCG | CTT | GTG | TTG | TAT | AGT | GTG | CAA | GGG | 2400 |
| Phe | Leu | Met | Ile | Gly | Ile | Val | Ser | Leu | Val | Leu | Tyr | Ser | Val | Gln | Gly | |
| 785 | | | | | 790 | | | | | 795 | | | | | 800 | |
| ACC | TTG | TTT | GCA | TAT | AGT | TCC | GAA | AAG | ATG | GTC | TAC | CGG | GCC | CGC | AGT | 2448 |
| Thr | Leu | Phe | Ala | Tyr | Ser | Ser | Glu | Lys | Met | Val | Tyr | Arg | Ala | Arg | Ser | |
| | | | | 805 | | | | | 810 | | | | | 815 | | |
| CAA | GCA | TTC | CGG | GTG | ATA | CTG | CAC | CAG | GAT | ATC | TCT | TTC | TTC | GAT | CAA | 2496 |
| Gln | Ala | Phe | Arg | Val | Ile | Leu | His | Gln | Asp | Ile | Ser | Phe | Phe | Asp | Gln | |
| | | | 820 | | | | | 825 | | | | | 830 | | | |
| CAG | GAA | AAC | ACG | ACA | GGC | GCA | TTA | ACA | GCC | ACT | CTG | AGC | GCG | GGG | ACC | 2544 |
| Gln | Glu | Asn | Thr | Thr | Gly | Ala | Leu | Thr | Ala | Thr | Leu | Ser | Ala | Gly | Thr | |
| | | 835 | | | | | 840 | | | | | 845 | | | | |
| AAA | GAA | CTA | ACT | GGC | ATT | AGT | GGC | GTC | ACA | TTG | GGG | ACT | ATC | TTG | ATT | 2592 |
| Lys | Glu | Leu | Thr | Gly | Ile | Ser | Gly | Val | Thr | Leu | Gly | Thr | Ile | Leu | Ile | |
| | 850 | | | | | 855 | | | | | 860 | | | | | |
| GTC | TCT | GTC | AAT | CTT | GTG | GCT | TCC | TTG | GGG | GTA | GCC | CTT | GTA | ATA | GGC | 2640 |
| Val | Ser | Val | Asn | Leu | Val | Ala | Ser | Leu | Gly | Val | Ala | Leu | Val | Ile | Gly | |
| 865 | | | | | 870 | | | | | 875 | | | | | 880 | |
| TGG | AAG | TTG | GCA | CTG | GTG | TGC | ATC | TCC | GCG | GTT | CCA | GCC | CTG | CTG | ATG | 2688 |
| Trp | Lys | Leu | Ala | Leu | Val | Cys | Ile | Ser | Ala | Val | Pro | Ala | Leu | Leu | Met | |
| | | | | 885 | | | | | 890 | | | | | 895 | | |
| TGT | GGA | TTT | GTT | CGC | GTT | TGG | ATG | TTG | GAG | CGG | TTC | CAA | CGA | AGG | GCC | 2736 |
| Cys | Gly | Phe | Val | Arg | Val | Trp | Met | Leu | Glu | Arg | Phe | Gln | Arg | Arg | Ala | |
| | | | | 900 | | | | | 905 | | | | | 910 | | |
| AAG | AAA | GCA | TAT | CAA | GAA | TCA | GCT | AGT | TCT | GCT | TGT | GAG | GCA | GCC | TCT | 2784 |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| Lys | Lys | Ala | Tyr | Gln | Glu | Ser | Ala | Ser | Ser | Ala | Cys | Glu | Ala | Ala | Ser |      |
|     |     | 915 |     |     |     |     | 920 |     |     |     | 925 |     |     |     |     |      |
| GCC | ATC | CGT | ACG | GTC | GTT | TCT | TTG | ACC | ATG | GAG | ACG | GAG | GCT | TTG | CAA | 2832 |
| Ala | Ile | Arg | Thr | Val | Val | Ser | Leu | Thr | Met | Glu | Thr | Glu | Ala | Leu | Gln |      |
|     | 930 |     |     |     |     | 935 |     |     |     |     | 940 |     |     |     |     |      |
| TCC | TAT | CAA | GCA | CAG | CTC | CGT | CGG | CAG | CTG | AAG | AGT | GAT | ATA | CTC | CCC | 2880 |
| Ser | Tyr | Gln | Ala | Gln | Leu | Arg | Arg | Gln | Leu | Lys | Ser | Asp | Ile | Leu | Pro |      |
| 945 |     |     |     |     | 950 |     |     |     |     | 955 |     |     |     |     | 960 |      |
| ATT | GTG | AAA | TCG | TCC | TTA | CTC | TAC | GCC | AGC | TCA | CAG | GCG | TTG | CCT | TTC | 2928 |
| Ile | Val | Lys | Ser | Ser | Leu | Leu | Tyr | Ala | Ser | Ser | Gln | Ala | Leu | Pro | Phe |      |
|     |     |     |     | 965 |     |     |     |     | 970 |     |     |     |     | 975 |     |      |
| TTC | TGC | ATG | GCG | TTG | GGG | TTC | TGG | TAT | GGC | GGG | TCT | CTA | CTT | GGT | CAT | 2976 |
| Phe | Cys | Met | Ala | Leu | Gly | Phe | Trp | Tyr | Gly | Gly | Ser | Leu | Leu | Gly | His |      |
|     |     |     | 980 |     |     |     |     | 985 |     |     |     |     |     | 990 |     |      |
| GGA | GAG | TAT | TCC | CTG | TTT | CAA | TTT | TAC | GTG | TGC | TTC | AGT | GAG | GTG | ATC | 3024 |
| Gly | Glu | Tyr | Ser | Leu | Phe | Gln | Phe | Tyr | Val | Cys | Phe | Ser | Glu | Val | Ile |      |
|     |     | 995 |     |     |     |     | 1000 |    |     |     |     | 1005 |    |     |     |      |
| TTT | GGG | GCC | CAA | GCC | GCT | GGA | ACG | GTT | TTC | TCT | CAT | GCC | CCG | GAT | ATG | 3072 |
| Phe | Gly | Ala | Gln | Ala | Ala | Gly | Thr | Val | Phe | Ser | His | Ala | Pro | Asp | Met |      |
| 1010|     |     |     |     | 1015|     |     |     |     | 1020|     |     |     |     |     |      |
| GGA | AAG | GCG | AAG | CAC | GCT | GCC | CGT | GAG | TTC | AAA | CGT | CTG | TTC | AGC | AGC | 3120 |
| Gly | Lys | Ala | Lys | His | Ala | Ala | Arg | Glu | Phe | Lys | Arg | Leu | Phe | Ser | Ser |      |
| 1025|     |     |     |     | 1030|     |     |     |     | 1035|     |     |     |     | 1040|      |
| GAC | ACA | ATG | CAT | GCT | TCT | CGG | AGC | AAA | GGA | GTT | CCG | GTT | ACG | TCC | ATG | 3168 |
| Asp | Thr | Met | His | Ala | Ser | Arg | Ser | Lys | Gly | Val | Pro | Val | Thr | Ser | Met |      |
|     |     |     |     | 1045|     |     |     |     | 1050|     |     |     |     | 1055|     |      |
| CGA | GGA | CTG | GTG | GAG | TTC | CGC | GAT | GTC | TCC | TTT | CGA | TAT | CCC | AGT | CGC | 3216 |
| Arg | Gly | Leu | Val | Glu | Phe | Arg | Asp | Val | Ser | Phe | Arg | Tyr | Pro | Ser | Arg |      |
|     |     |     | 1060|     |     |     |     | 1065|     |     |     |     | 1070|     |     |      |
| TTG | GAA | CAA | CCA | ATC | CTT | CGC | CAC | TTG | AAC | CTG | ACC | ATC | AAG | CCA | GGG | 3264 |
| Leu | Glu | Gln | Pro | Ile | Leu | Arg | His | Leu | Asn | Leu | Thr | Ile | Lys | Pro | Gly |      |
|     |     |     | 1075|     |     |     |     | 1080|     |     |     |     | 1085|     |     |      |
| CAA | TTT | GTT | GCA | CTA | GTG | GGT | GCG | AGT | GGA | AGC | GGC | AAG | AGC | ACT | ACC | 3312 |
| Gln | Phe | Val | Ala | Leu | Val | Gly | Ala | Ser | Gly | Ser | Gly | Lys | Ser | Thr | Thr |      |
|     |     |     | 1090|     |     |     |     | 1095|     |     |     |     | 1100|     |     |      |
| ATT | GCG | TTG | CTG | GAG | AGA | TTC | TAT | GAT | CCC | CTC | AAA | GGT | GGT | GTT | TAC | 3360 |
| Ile | Ala | Leu | Leu | Glu | Arg | Phe | Tyr | Asp | Pro | Leu | Lys | Gly | Gly | Val | Tyr |      |
| 1105|     |     |     |     | 1110|     |     |     |     | 1115|     |     |     |     | 1120|      |
| GTA | GAT | GGA | AAG | AAT | ATT | ATC | ACT | CTC | GAG | ATG | TCT | TCC | TAT | CGC | AGT | 3408 |
| Val | Asp | Gly | Lys | Asn | Ile | Ile | Thr | Leu | Glu | Met | Ser | Ser | Tyr | Arg | Ser |      |
|     |     |     |     | 1125|     |     |     |     | 1130|     |     |     |     | 1135|     |      |
| CAC | TTG | GCT | CTC | ATT | AGC | CAA | GAA | CCG | ACT | TTG | TTC | CAA | GGG | ACC | ATC | 3456 |
| His | Leu | Ala | Leu | Ile | Ser | Gln | Glu | Pro | Thr | Leu | Phe | Gln | Gly | Thr | Ile |      |
|     |     |     | 1140|     |     |     |     | 1145|     |     |     |     | 1150|     |     |      |
| CGA | GAG | AAC | ATC | CTG | CTA | GGG | AGC | AAC | ACA | CCT | CAT | GTC | ACA | GAT | GAT | 3504 |
| Arg | Glu | Asn | Ile | Leu | Leu | Gly | Ser | Asn | Thr | Pro | His | Val | Thr | Asp | Asp |      |
|     |     |     | 1155|     |     |     |     | 1160|     |     |     |     | 1165|     |     |      |
| TTT | CTT | GTT | AAA | GCC | TGC | AAG | GAT | GCA | AAC | ATA | TAC | GAT | TTC | ATA | TTG | 3552 |
| Phe | Leu | Val | Lys | Ala | Cys | Lys | Asp | Ala | Asn | Ile | Tyr | Asp | Phe | Ile | Leu |      |
| 1170|     |     |     |     | 1175|     |     |     |     | 1180|     |     |     |     |     |      |
| TCA | TTG | CCG | CAA | GGC | TTC | AAC | ACC | ATT | GTT | GGC | AAT | AAG | GGA | GGC | ATG | 3600 |
| Ser | Leu | Pro | Gln | Gly | Phe | Asn | Thr | Ile | Val | Gly | Asn | Lys | Gly | Gly | Met |      |
| 1185|     |     |     |     | 1190|     |     |     |     | 1195|     |     |     |     | 1200|      |
| CTC | TCC | GGT | GGC | CAG | AAA | CAG | CGC | ATT | GCC | ATC | GCT | CGG | GCC | CTC | ATT | 3648 |
| Leu | Ser | Gly | Gly | Gln | Lys | Gln | Arg | Ile | Ala | Ile | Ala | Arg | Ala | Leu | Ile |      |
|     |     |     |     | 1205|     |     |     |     | 1210|     |     |     |     | 1215|     |      |
| CGG | AAT | CCA | AAA | ATC | CTC | CTG | TTG | GAC | GAG | GCT | ACG | TCC | GCG | CTA | GAT | 3696 |
| Arg | Asn | Pro | Lys | Ile | Leu | Leu | Leu | Asp | Glu | Ala | Thr | Ser | Ala | Leu | Asp |      |
|     |     |     | 1220|     |     |     |     | 1225|     |     |     |     | 1230|     |     |      |
| TCC | GAG | TCG | GAA | AAG | GTG | GTC | CAG | GCA | GCA | TTG | GAT | GCC | GCC | GCG | CGG | 3744 |

| | | | | | | | | | | | | | | | | |
|---|---|---|---|---|---|---|---|---|---|---|---|---|---|---|---|---|
| Ser | Glu | Ser | Glu | Lys | Val | Val | Gln | Ala | Ala | Leu | Asp | Ala | Ala | Ala | Arg | |
| | | 1235 | | | | 1240 | | | | | 1245 | | | | | |
| GGA | CGC | ACA | ACG | ATC | GCA | GTT | GCT | CAC | CGG | CTG | AGC | ACT | ATC | CAG | CGC | 3792 |
| Gly | Arg | Thr | Thr | Ile | Ala | Val | Ala | His | Arg | Leu | Ser | Thr | Ile | Gln | Arg | |
| 1250 | | | | | 1255 | | | | | 1260 | | | | | | |
| GCA | GAC | TTG | ATA | TAT | GTG | CTA | GAT | CAG | GGG | GAG | GTC | GTT | GAA | TCA | GGT | 3840 |
| Ala | Asp | Leu | Ile | Tyr | Val | Leu | Asp | Gln | Gly | Glu | Val | Val | Glu | Ser | Gly | |
| 1265 | | | | 1270 | | | | | 1275 | | | | | | 1280 | |
| ACG | CAC | CGG | GAA | CTT | CTC | CGG | AAG | AAG | GGA | CGC | TAC | TAC | GAA | CTC | GTC | 3888 |
| Thr | His | Arg | Glu | Leu | Leu | Arg | Lys | Lys | Gly | Arg | Tyr | Tyr | Glu | Leu | Val | |
| | | | | 1285 | | | | | 1290 | | | | | 1295 | | |
| CAT | CTA | CAG | AAT | CCG | GAT | GCC | ACG | GGT | ACG | AAG | TAG | | | | | 3924 |
| His | Leu | Gln | Asn | Pro | Asp | Ala | Thr | Gly | Thr | Lys | | | | | | |
| | | | 1300 | | | | | 1305 | | | | | | | | |

(2) INFORMATION FOR SEQ ID NO:2:

(i) SEQUENCE CHARACTERISTICS:
        (A) LENGTH: 1307 amino acids
        (B) TYPE: amino acid
        (D) TOPOLOGY: linear     (ii) MOLECULE TYPE: protein     (xi) SEQUENCE DESCRIPTION: SEQ ID NO:2:

| | | | | | | | | | | | | | | |
|---|---|---|---|---|---|---|---|---|---|---|---|---|---|---|
| Met | Lys | Ser | Asp | Lys | Asp | Ile | Leu | Met | Lys | Pro | Leu | Pro | Lys | Ser | Pro |
| 1 | | | | 5 | | | | | 10 | | | | | 15 | |
| Gly | Thr | Gly | Ser | Thr | Thr | Thr | Gly | His | Ser | Val | Ser | His | Ala | Glu | Glu |
| | | | | 20 | | | | | 25 | | | | | 30 | |
| Val | Leu | Asp | Arg | Gln | Leu | His | Thr | Pro | Val | Ser | Gln | Ile | Gly | Phe | Phe |
| | | | | 35 | | | | | 40 | | | | | 45 | |
| Gly | Ile | Tyr | Arg | Tyr | Ala | Thr | Arg | Trp | Asp | Val | Ala | Ile | Leu | Phe | Gly |
| | | | 50 | | | | | 55 | | | | | 60 | | |
| Ser | Ala | Leu | Ala | Ala | Ile | Ala | Gly | Gly | Ala | Ala | Leu | Pro | Leu | Phe | Thr |
| 65 | | | | | 70 | | | | | 75 | | | | | 80 |
| Val | Leu | Phe | Gly | Arg | Leu | Thr | Ser | Thr | Phe | Gln | Asp | Ile | Ala | Thr | His |
| | | | | 85 | | | | | 90 | | | | | 95 | |
| Arg | Ile | Thr | Tyr | Asp | His | Phe | His | His | Glu | Leu | Thr | Lys | Asn | Val | Val |
| | | | 100 | | | | | 105 | | | | | 110 | | |
| Tyr | Phe | Ile | Tyr | Leu | Gly | Ala | Ala | Glu | Phe | Val | Ala | Ile | Tyr | Leu | Ala |
| | | | 115 | | | | | 120 | | | | | 125 | | |
| Thr | Val | Gly | Phe | Ile | Tyr | Thr | Gly | Asp | His | Val | Val | Gln | Gln | Ile | Arg |
| | | 130 | | | | | 135 | | | | | 140 | | | |
| Val | Glu | Tyr | Phe | Gln | Ala | Ile | Leu | Arg | Gln | Asn | Ile | Ala | Phe | Phe | Asp |
| 145 | | | | | 150 | | | | | 155 | | | | | 160 |
| Thr | Leu | Gly | Ala | Gly | Glu | Ile | Thr | Thr | Arg | Ile | Thr | Ala | Asp | Thr | Asn |
| | | | | 165 | | | | | 170 | | | | | 175 | |
| Leu | Ile | Gln | Asp | Gly | Ile | Ser | Glu | Lys | Val | Gly | Leu | Ala | Leu | Thr | Gly |
| | | | 180 | | | | | 185 | | | | | 190 | | |
| Leu | Ser | Thr | Phe | Val | Thr | Ala | Phe | Ile | Ile | Ala | Tyr | Ile | Lys | Asn | Trp |
| | | | 195 | | | | | 200 | | | | | 205 | | |
| Lys | Leu | Ala | Leu | Ile | Cys | Ser | Ala | Ser | Leu | Leu | Ala | Leu | Leu | Leu | Thr |
| | | 210 | | | | | 215 | | | | | 220 | | | |
| Met | Gly | Gly | Cys | Ser | Thr | Leu | Met | Leu | Ile | Phe | Ser | Lys | Lys | Ala | Leu |
| 225 | | | | | 230 | | | | | 235 | | | | | 240 |
| Glu | Tyr | Gln | Gly | Arg | Gly | Ala | Ser | Met | Ala | Glu | Asp | Ile | Leu | Asp | Ser |
| | | | | 245 | | | | | 250 | | | | | 255 | |
| Ile | Arg | Thr | Val | Ala | Ala | Phe | Asn | Ala | Gln | Glu | Thr | Leu | Ala | Arg | Lys |

|     |     |     |     |     |     |     |     |     |     |     |     |     |     |     |
| --- | --- | --- | --- | --- | --- | --- | --- | --- | --- | --- | --- | --- | --- | --- |
|     |     |     |     |     | 260 |     |     |     |     | 265 |     |     |     | 270 |
| Tyr | Glu | Ser | His | Leu | Lys | Asp | Ala | Glu | Gly | Pro | Gly | Met | Lys | Ser | Lys |
|     |     | 275 |     |     |     | 280 |     |     |     |     | 285 |     |     |     |
| Val | Ile | Phe | Ala | Ile | Met | Val | Gly | Ala | Leu | Leu | Cys | Ile | Met | Tyr | Leu |
|     | 290 |     |     |     | 295 |     |     |     |     | 300 |     |     |     |     |
| Asn | Tyr | Gly | Leu | Gly | Phe | Trp | Met | Gly | Ser | Arg | Phe | Leu | Val | Glu | Gly |
| 305 |     |     |     |     | 310 |     |     |     | 315 |     |     |     |     |     | 320 |
| Ile | Ser | Asn | Ile | Lys | Ala | Gly | Asp | Val | Leu | Thr | Ile | Met | Met | Ala | Ile |
|     |     |     |     | 325 |     |     |     |     | 330 |     |     |     |     | 335 |     |
| Ile | Leu | Gly | Ser | Tyr | Asn | Leu | Gly | Asn | Val | Ala | Pro | Asn | Gly | Gln | Ala |
|     |     |     | 340 |     |     |     |     | 345 |     |     |     |     | 350 |     |     |
| Leu | Ser | Asp | Ala | Val | Ala | Ala | Ser | Lys | Leu | Tyr | Gly | Thr | Ile | Asp |
|     |     | 355 |     |     |     | 360 |     |     |     |     | 365 |     |     |     |
| Arg | Gln | Ser | Pro | Leu | Asp | Ala | Leu | Ser | Asp | Gln | Gly | Lys | Thr | Leu | Glu |
|     | 370 |     |     |     |     | 375 |     |     |     |     | 380 |     |     |     |     |
| Phe | Val | Arg | Gly | Asn | Ile | Val | Leu | Gln | Asn | Ile | Arg | His | Val | Tyr | Pro |
| 385 |     |     |     |     | 390 |     |     |     |     | 395 |     |     |     |     | 400 |
| Ser | Arg | Pro | Glu | Val | Thr | Val | Ala | His | Asp | Leu | Ser | Cys | Tyr | Ile | Pro |
|     |     |     |     | 405 |     |     |     |     | 410 |     |     |     |     | 415 |     |
| Ala | Gly | Lys | Thr | Thr | Ala | Phe | Val | Gly | Pro | Ser | Gly | Ser | Gly | Lys | Ser |
|     |     |     | 420 |     |     |     |     |     | 425 |     |     |     | 430 |     |     |
| Thr | Ile | Ile | Ser | Leu | Leu | Glu | Arg | Phe | Tyr | Asp | Pro | Val | Ala | Gly | Thr |
|     |     | 435 |     |     |     |     | 440 |     |     |     |     |     | 445 |     |     |
| Ile | Met | Leu | Asp | Gly | His | Asp | Ile | Gln | Thr | Leu | Asn | Leu | Arg | Trp | Leu |
|     | 450 |     |     |     |     | 455 |     |     |     |     | 460 |     |     |     |     |
| Arg | Gln | Gln | Met | Ser | Leu | Val | Ser | Gln | Glu | Pro | Arg | Leu | Phe | Ala | Thr |
| 465 |     |     |     |     | 470 |     |     |     |     | 475 |     |     |     |     | 480 |
| Thr | Ile | Ala | Glu | Asn | Ile | Arg | Tyr | Gly | Ile | Ile | Gly | Ser | Arg | Phe | Glu |
|     |     |     |     | 485 |     |     |     |     | 490 |     |     |     |     | 495 |     |
| Lys | Glu | Ser | Thr | Tyr | Glu | Ile | Arg | Lys | Arg | Val | Glu | Ala | Ala | Ala | Arg |
|     |     |     | 500 |     |     |     |     | 505 |     |     |     |     | 510 |     |     |
| Met | Ala | Asn | Ala | His | Asp | Phe | Ile | Met | Ala | Leu | Pro | Asn | Gly | Tyr | Asp |
|     |     |     | 515 |     |     |     |     | 520 |     |     |     |     | 525 |     |     |
| Thr | Asn | Ile | Glu | Ser | Phe | Ser | Leu | Ser | Gly | Gly | Gln | Lys | Gln | Arg | Ile |
|     |     | 530 |     |     |     |     | 535 |     |     |     |     | 540 |     |     |     |
| Ala | Ile | Ala | Arg | Ala | Ile | Ile | Lys | Asp | Pro | Lys | Ile | Leu | Leu | Leu | Asp |
| 545 |     |     |     |     | 550 |     |     |     |     | 555 |     |     |     |     | 560 |
| Glu | Ala | Thr | Ser | Ala | Leu | Asp | Thr | Lys | Ser | Glu | Lys | Leu | Val | Gln | Ala |
|     |     |     |     | 565 |     |     |     |     | 570 |     |     |     |     | 575 |     |
| Ala | Leu | Asp | Lys | Ala | Ser | Lys | Gly | Arg | Thr | Thr | Ile | Val | Ile | Ala | His |
|     |     |     | 580 |     |     |     |     | 585 |     |     |     |     | 590 |     |     |
| Arg | Leu | Ser | Thr | Ile | Gln | Lys | Ala | Tyr | Asn | Ile | Ile | Val | Leu | Ala | Asn |
|     |     | 595 |     |     |     |     | 600 |     |     |     |     | 605 |     |     |     |
| Gly | Gln | Ile | Val | Glu | Gln | Gly | Pro | His | Glu | His | Leu | Met | Asp | Arg | Arg |
|     |     | 610 |     |     |     |     | 615 |     |     |     |     | 620 |     |     |     |
| Gly | Ile | Tyr | Cys | Asp | Met | Val | Glu | Ala | His | Glu | Ile | Lys | Lys | Arg | Tyr |
| 625 |     |     |     |     | 630 |     |     |     |     | 635 |     |     |     |     | 640 |
| Ser | Arg | Tyr | Ser | Lys | Arg | Tyr | Ser | Gln | Leu | Leu | Thr | Asn | Leu | Ser | Pro |
|     |     |     |     | 645 |     |     |     |     | 650 |     |     |     |     | 655 |     |
| Lys | His | Asn | Pro | Met | Thr | Phe | Phe | Asp | Lys | Asp | Tyr | Pro | Gly | Asp |
|     |     |     | 660 |     |     |     |     | 665 |     |     |     | 670 |     |     |
| Asp | Glu | Ser | Asp | Ile | Tyr | Ser | Ile | Leu | Ser | Asp | Asp | Ala | Ser | Asp | Ile |
|     |     |     | 675 |     |     |     |     | 680 |     |     |     |     | 685 |     |     |

| | | | | | | | | | | | | | | |
|---|---|---|---|---|---|---|---|---|---|---|---|---|---|---|
|Gly|Leu|His|Thr|Gly|Glu|Lys|Gln|Arg|Pro|Val|Ser|Arg|Met|Ser|Leu|
| |690| | | | |695| | | |700| | | | | |
|Ser|His|Leu|Met|Gln|Pro|Val|Lys|Glu|Glu|Ala|Tyr|Ser|Phe|Trp|Thr|
|705| | | | |710| | | |715| | | | | |720|
|Leu|Phe|Lys|Phe|Leu|Ala|Ser|Phe|Asn|Arg|Pro|Glu|Trp|Pro|Phe|Leu|
| | | | |725| | | |730| | | | |735| | |
|Leu|Leu|Gly|Leu|Cys|Ala|Ser|Ile|Leu|Ala|Gly|Gly|Ile|Gln|Pro|Ser|
| | | |740| | | |745| | | | |750| | | |
|Gln|Ala|Val|Leu|Phe|Ala|Lys|Ala|Val|Ser|Thr|Leu|Ser|Leu|Pro|Pro|
| | |755| | | |760| | | | |765| | | | |
|Leu|Glu|Tyr|Pro|Lys|Leu|Arg|His|Asp|Ala|Asn|Phe|Trp|Cys|Leu|Met|
| |770| | | |775| | | | |780| | | | | |
|Phe|Leu|Met|Ile|Gly|Ile|Val|Ser|Leu|Val|Leu|Tyr|Ser|Val|Gln|Gly|
|785| | | |790| | | | |795| | | | | |800|
|Thr|Leu|Phe|Ala|Tyr|Ser|Ser|Glu|Lys|Met|Val|Tyr|Arg|Ala|Arg|Ser|
| | | | |805| | | |810| | | | |815| | |
|Gln|Ala|Phe|Arg|Val|Ile|Leu|His|Gln|Asp|Ile|Ser|Phe|Phe|Asp|Gln|
| | | |820| | | |825| | | | |830| | | |
|Gln|Glu|Asn|Thr|Thr|Gly|Ala|Leu|Thr|Ala|Thr|Leu|Ser|Ala|Gly|Thr|
| | |835| | | | |840| | | | |845| | | |
|Lys|Glu|Leu|Thr|Gly|Ile|Ser|Gly|Val|Thr|Leu|Gly|Thr|Ile|Leu|Ile|
| |850| | | | |855| | | |860| | | | | |
|Val|Ser|Val|Asn|Leu|Val|Ala|Ser|Leu|Gly|Val|Ala|Leu|Val|Ile|Gly|
|865| | | |870| | | | |875| | | | | |880|
|Trp|Lys|Leu|Ala|Leu|Val|Cys|Ile|Ser|Ala|Val|Pro|Ala|Leu|Leu|Met|
| | | |885| | | | |890| | | | |895| | |
|Cys|Gly|Phe|Val|Arg|Val|Trp|Met|Leu|Glu|Arg|Phe|Gln|Arg|Arg|Ala|
| | |900| | | | |905| | | | |910| | | |
|Lys|Lys|Ala|Tyr|Gln|Glu|Ser|Ala|Ser|Ala|Cys|Glu|Ala|Ala|Ser|
| | |915| | | |920| | | | |925| | | | |
|Ala|Ile|Arg|Thr|Val|Val|Ser|Leu|Thr|Met|Glu|Thr|Glu|Ala|Leu|Gln|
| |930| | | | |935| | | | |940| | | | |
|Ser|Tyr|Gln|Ala|Gln|Leu|Arg|Arg|Gln|Leu|Lys|Ser|Asp|Ile|Leu|Pro|
|945| | | | |950| | | | |955| | | | |960|
|Ile|Val|Lys|Ser|Ser|Leu|Leu|Tyr|Ala|Ser|Ser|Gln|Ala|Leu|Pro|Phe|
| | | |965| | | | |970| | | | |975| | |
|Phe|Cys|Met|Ala|Leu|Gly|Phe|Trp|Tyr|Gly|Gly|Ser|Leu|Leu|Gly|His|
| | | |980| | | |985| | | | |990| | | |
|Gly|Glu|Tyr|Ser|Leu|Phe|Gln|Phe|Tyr|Val|Cys|Phe|Ser|Glu|Val|Ile|
| | |995| | | |1000| | | |1005| | | | |
|Phe|Gly|Ala|Gln|Ala|Ala|Gly|Thr|Val|Phe|Ser|His|Ala|Pro|Asp|Met|
|1010| | | | |1015| | | | |1020| | | | | |
|Gly|Lys|Ala|Lys|His|Ala|Ala|Arg|Glu|Phe|Lys|Arg|Leu|Phe|Ser|Ser|
|1025| | | | |1030| | | | |1035| | | | |1040|
|Asp|Thr|Met|His|Ala|Ser|Arg|Ser|Lys|Gly|Val|Pro|Val|Thr|Ser|Met|
| | | | |1045| | | | |1050| | | | |1055| |
|Arg|Gly|Leu|Val|Glu|Phe|Arg|Asp|Val|Ser|Phe|Arg|Tyr|Pro|Ser|Arg|
| | | |1060| | | | |1065| | | | |1070| | |
|Leu|Glu|Gln|Pro|Ile|Leu|Arg|His|Leu|Asn|Leu|Thr|Ile|Lys|Pro|Gly|
| | | |1075| | | | |1080| | | | |1085| | |
|Gln|Phe|Val|Ala|Leu|Val|Gly|Ala|Ser|Gly|Ser|Gly|Lys|Ser|Thr|Thr|
| |1090| | | | |1095| | | | |1100| | | | |
|Ile|Ala|Leu|Leu|Glu|Arg|Phe|Tyr|Asp|Pro|Leu|Lys|Gly|Gly|Val|Tyr|
|1105| | | | |1110| | | | |1115| | | | |1120|

-continued

| | | | | | | | | | | | | | | |
|---|---|---|---|---|---|---|---|---|---|---|---|---|---|---|
| Val | Asp | Gly | Lys | Asn<br>1125 | Ile | Ile | Thr | Leu | Glu<br>1130 | Met | Ser | Ser | Tyr | Arg Ser<br>1135 |
| His | Leu | Ala | Leu<br>1140 | Ile | Ser | Gln | Glu | Pro<br>1145 | Thr | Leu | Phe | Gln | Thr<br>1150 | Ile |
| Arg | Glu | Asn<br>1155 | Ile | Leu | Leu | Gly | Ser<br>1160 | Asn | Thr | Pro | His | Val<br>1165 | Thr | Asp Asp |
| Phe | Leu<br>1170 | Val | Lys | Ala | Cys | Lys<br>1175 | Asp | Ala | Asn | Ile | Tyr<br>1180 | Asp | Phe | Ile Leu |
| Ser | Leu | Pro | Gln | Gly | Phe<br>1190 | Asn | Thr | Ile | Val | Gly<br>1195 | Asn | Lys | Gly | Gly Met |
| 1185 | | | | | | | | | | | | | | 1200 |
| Leu | Ser | Gly | Gly | Gln<br>1205 | Lys | Gln | Arg | Ile | Ala<br>1210 | Ile | Ala | Arg | Ala | Leu Ile<br>1215 |
| Arg | Asn | Pro | Lys<br>1220 | Ile | Leu | Leu | Leu | Asp<br>1225 | Glu | Ala | Thr | Ser | Ala<br>1230 | Leu Asp |
| Ser | Glu | Ser<br>1235 | Glu | Lys | Val | Val | Gln<br>1240 | Ala | Ala | Leu | Asp | Ala<br>1245 | Ala | Ala Arg |
| Gly | Arg<br>1250 | Thr | Thr | Ile | Ala | Val<br>1255 | Ala | His | Arg | Leu | Ser<br>1260 | Thr | Ile | Gln Arg |
| Ala | Asp | Leu | Ile | Tyr<br>1270 | Val | Leu | Asp | Gln | Gly | Glu<br>1275 | Val | Val | Glu | Ser Gly |
| 1265 | | | | | | | | | | | | | | 1280 |
| Thr | His | Arg | Glu | Leu<br>1285 | Leu | Arg | Lys | Lys | Gly<br>1290 | Arg | Tyr | Tyr | Glu | Leu Val<br>1295 |
| His | Leu | Gln | Asn | Pro<br>1300 | Asp | Ala | Thr | Gly<br>1305 | Thr | Lys | | | | |

( 2 ) INFORMATION FOR SEQ ID NO:3:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( i i ) MOLECULE TYPE: DNA     ( x i ) SEQUENCE DESCRIPTION: SEQ ID NO:3:

TATCTATCGA TATGCGACTC G                                                                                      21

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( i i ) MOLECULE TYPE: DNA     ( x i ) SEQUENCE DESCRIPTION: SEQ ID NO:4:

GTAGACCACA TTCTTGGTCA G                                                                                      21

MULTIPLE DRUG RESISTANCE GENE OF ASPERGILLUS FLAVUS

TECHNICAL FIELD OF THE INVENTION

This invention relates to recombinant DNA technology. In particular, the invention concerns the cloning of nucleic acid encoding a multiple drug resistance protein of *Aspergillus flavus*.

BACKGROUND OF THE INVENTION

Multiple drug resistance (MDR) mediated by the human mdr-1 gene product was initially recognized during the course of developing regimens for cancer chemotherapy (Fojo et al., 1987, *Journal of Clinical Oncology* 5:1922–1927). A multiple drug resistant cancer cell line exhibits resistance to high levels of a large variety of cytotoxic compounds. Frequently these cytotoxic compounds will have no common structural features nor will they interact with a common target within the cell. Resistance to these cytotoxic agents is mediated by an outward directed, ATP-dependent pump encoded by the mdr-1 gene. By this mechanism, toxic levels of a particular cytotoxic compound are not allowed to accumulate within the cell.

MDR-like genes have been identified in a number of divergent organisms including numerous bacterial species, the fruit fly *Drosophila melanogaster*, *Plasmodium falciparum*, the yeast *Saccharomyces cerevisiae*, *Caenorhabditis elegans*, *Leishmania donovanii*, marine sponges, the plant *Arabidopsis thaliana*, as well as *Homo sapiens*. Extensive searches have revealed several classes of compounds that are able to reverse the MDR phenotype of multiple drug resistant human cancer cell lines rendering them susceptible to the effects of cytotoxic compounds. These compounds, referred to herein as "MDR inhibitors", include for example, calcium channel blockers, anti-arrhythmics, antihypertensives, antibiotics, antihistamines, immuno-suppressants, steroid hormones, modified steroids, lipophilic cations, diterpenes, detergents, antidepressants, and antipsychotics (Gottesman and Pastan, 1993, *Annual Review of Biochemistry* 62:385–427). Clinical application of human MDR inhibitors to cancer chemotherapy has become an area of intensive focus for research.

On another front, the discovery and development of antifungal compounds for specific fungal species has also met with some degree of success. Candida species represent the majority of fungal infections, and screens for new antifungal compounds have been designed to discover anti-Candida compounds. During development of antifungal agents, activity has generally been optimized based on activity against *Candida albicans*. As a consequence, these anti-Candida compounds frequently do not possess clinically significant activity against other fungal species such as *Aspergillus flavus*. However, it is interesting to note that at higher concentrations some anti-Candida compounds are able to kill Aspergillus fungal species. This suggests that the antifungal target(s) of these anti-Candida compounds is present in Aspergillus as well. Such results indicate that Aspergillus may possess a natural mechanism of resistance that permits them to survive in clinically relevant concentrations of antifungal compounds. Until the present invention, such a general mechanism of resistance to antifungal compounds in *Aspergillus flavus* has remained undescribed.

SUMMARY OF THE INVENTION

The invention provides, inter alia, isolated nucleic acid molecules that comprise nucleic acid encoding a multiple drug resistance protein from *Aspergillus flavus*, known as Afl-MDR1, vectors encoding Afl-MDR1, and host cells transformed with these vectors.

In another embodiment, the invention provides a method for determining the fungal MDR inhibition activity of a compound which comprises:

a) growing a culture of yeast cells, transformed with a vector which provides expression of Afl-MDR1, in the presence of:
   (i) an antifungal agent to which said yeast cell is resistant, but to which said yeast cell is sensitive in its untransformed state;
   (ii) a compound suspected of possessing fungal MDR inhibition activity; and
b) determining the fungal MDR inhibition activity of said compound by measuring the ability of the antifungal agent to inhibit the growth of said yeast cell.

BRIEF DESCRIPTION OF THE FIGURES

The restriction enzyme site and function maps presented in the accompanying drawings are approximate representations of plasmid pPSR-6 and plasmid pPSR-8, discussed herein. The restriction enzyme site information is not exhaustive. There may be more restriction enzyme sites of a given type on the vectors than actually shown on the maps.

DETAILED DESCRIPTION OF THE INVENTION

The present invention provides isolated nucleic acid molecules that comprise a nucleic acid sequence encoding Afl-MDR1. The amino acid sequence of Afl-MDR1 is provided in the Sequence Listing as SEQ ID NO: 2. The cDNA (complementary deoxyribonucleic acid) sequence encoding Afl-MDR1 is provided in the Sequence Listing as SEQ ID NO: 1.

Those skilled in the art will recognize that the degenerate nature of the genetic code enables one to construct many different nucleic acid sequences that encode the amino acid sequence of SEQ ID NO: 2. The cDNA sequence depicted by SEQ ID NO: 1 is only one of many possible Afl-MDR1 encoding sequences. Consequently, the constructions described below and in the accompanying examples for the preferred nucleic acid molecules, vectors, and transformants of the invention are illustrative and are not intended to limit the scope of the invention.

All nucleotide and amino acid abbreviations used in this disclosure are those accepted by the United States Patent and Trademark Office as set forth in 37 C. F. R. §1.822(b)(1994)

The term "vector" refers to any autonomously replicating or integrating agent, including but not limited to plasmids, cosmids, and viruses (including phage), comprising a nucleic acid molecule to which one or more additional nucleic acid molecules can be added. Included in the definition of "vector" is the term "expression vector". Vectors are used either to amplify and/or to express deoxyribonucleic acid (DNA), either genomic or cDNA, or RNA (ribonucleic acid) which encodes Afl-MDR1, or to amplify DNA or RNA that hybridizes with DNA or RNA encoding Afl-MDR1.

The term "expression vector" refers to vectors which comprise a transcriptional promoter (hereinafter "promoter") and other regulatory sequences positioned to drive expression of a DNA segment that encodes Afl-MDR1. Expression vectors of the present invention are replicable DNA constructs in which a DNA sequence encoding Afl-MDR1 is operably linked to suitable control sequences capable of effecting the expression of Afl-MDR1 in a suitable host. Such control sequences include a promoter, an optional operator sequence to control transcription, a sequence encoding suitable mRNA ribosomal binding sites, and sequences which control termination of transcription and translation. DNA regions are operably linked when they are functionally related to each other. For example, a promoter is operably linked to a DNA coding sequence if it controls the transcription of the sequence, or a ribosome binding site is operably linked to a coding sequence if it is positioned so as to permit translation.

The term "MDR inhibition activity" refers to the ability of a compound to inhibit the MDR activity of a host cell, thereby increasing the antifungal activity of an antifungal compound against said host cell.

In the present invention, Afl-MDR1 may be synthesized by host cells transformed with vectors that provide for the expression of DNA encoding Afl-MDR1. The DNA encoding Afl-MDR1 may be the natural sequence or a synthetic sequence or a combination of both ("semi-synthetic sequence"). The in vitro or in vivo transcription and translation of these sequences results in the production of Afl-MDR1. Synthetic and semi-synthetic sequences encoding Afl-MDR1 may be constructed by techniques well known in the art. See Brown et al. (1979) *Methods in Enzymology*, Academic Press, N.Y., 68:109–151. Afl-MDR1-encoding DNA, or portions thereof, may be generated using a conventional DNA synthesizing apparatus such as the Applied Biosystems Model 380A or 380B DNA synthesizers (commercially available from Applied Biosystems, Inc., 850 Lincoln Center Drive, Foster City, Calif. 94404).

Owing to the natural degeneracy of the genetic code, the skilled artisan will recognize that a sizable yet definite number of nucleic acid sequences may be constructed which encode Afl-MDR1. All such nucleic acid sequences are provided by the present invention. These sequences can be prepared by a variety of methods and, therefore, the invention is not limited to any particular preparation means. The nucleic acid sequences of the invention can be produced by a number of procedures, including DNA synthesis, cDNA cloning, genomic cloning, polymerase chain reaction (PCR) technology, or a combination of these approaches. These and other techniques are described by Maniatis, et al. *Molecular Cloning: A Laboratory Manual*, Cold Spring Harbor Press, Cold Spring Harbor Laboratory, Cold Spring Harbor, N.Y. (1989), or *Current Protocols in Molecular Biology* (F. M. Ausbel et al., 1989). The contents of both of these references are incorporated herein by reference.

In another aspect, this invention provides the genomic DNA encoding the Afl-MDR1. This DNA sequence is preferably obtained from plasmid pPSR-6. Plasmid pPSR-6 can be obtained from the host cell *Escherichia Coli* XL1-Blue/pPSR-6 which was deposited in the permanent culture collection of the Northern Regional Research Laboratory (NRRL), United States Department of Agriculture Service, 1815 North University Street, Peoria, Ill. 61604, on Feb. 10, 1995, and is available under accession number NRRL B-21406. A restriction site and function map of pPSR-6 is provided as FIG. 1 of the drawings. Plasmid pPSR-6 comprises the ColE1 origin of replication (ColE1) which allows replication in *Escherichia coli* host cells, and the ampicillin resistance gene (Amp) for selection of *E. coli* cells transformed with the plasmid grown in the presence of ampicillin. The plasmid also contains the T7 promoter and the origin of replication form the f1 filamentous phage. The genomic DNA encoding Afl-MDR1 can be obtained from plasmid pPSR-6 on an approximately 7.5 kilobase pair EcoRI restriction enzyme fragment.

Examination of the genomic DNA sequence encoding Afl-MDR1 suggested the presence of introns. The precise location of suspected introns was determined by comparing the cDNA sequence encoding Afl-MDR1 to the sequence of the genomic DNA encoding Afl-MDR1. The cDNA sequence was obtained in the following manner. Messenger RNA (mRNA) isolated from *Aspergillus flavus* was converted to cDNA by conventional methodologies. Polymerase Chain Reaction (PCR) primers were designed to amplify regions of the gene encoding Afl-MDR1 suspected to contain introns. These regions were amplified from Afl-MDR1 encoding cDNA using standard PCR methodologies. The PCR fragments generated from Afl-MDR1 encoding cDNA were subcloned into the vector pCRScript™ (Stratagene, Inc.). The DNA sequence of the subcloned DNA was determined using the dideoxy sequencing method. The cDNA sequence, which lacks introns, was then compared to the genomic DNA sequence to locate the precise position of the introns in the genomic DNA.

To effect the translation of Afl-MDR1 encoding DNA, one inserts the natural, synthetic, or semi-synthetic Afl-MDR1 encoding DNA sequence into any of a large number of appropriate expression vectors through the use of appropriate restriction endonucleases and DNA ligases. Synthetic and semi-synthetic Afl-MDR1 encoding DNA sequences can be designed, and natural Afl-MDR1 encoding nucleic acid can be modified, to possess restriction endonuclease cleavage sites to facilitate isolation from and integration into these vectors. Particular restriction endonucleases employed will be dictated by the restriction endonuclease cleavage pattern of the expression vector utilized. Restriction enzyme sites are chosen so as to properly orient the Afl-MDR1 encoding DNA with the control sequences to achieve proper in-frame transcription and translation of the Afl-MDR1 molecule. The Afl-MDR1 encoding DNA must be positioned so as to be in proper reading frame with the promoter and ribosome binding site of the expression vector, both of which are functional in the host cell in which Afl-MDR1 is to be expressed.

Expression of Afl-MDR1 in yeast cells, such as *Saccharomyces cerevisiae* is preferred. Suitable promoter sequences for use with yeast hosts include the promoters for 3-phosphoglycerate kinase (found on plasmid pAP12BD ATCC 53231 and described in U.S. Pat. No. 4,935,350, Jun. 19, 1990) or other glycolytic enzymes such as enolase (found on plasmid pAC1 ATCC 39532), glyceraldehyde-3-phosphate dehydrogenase (derived from plasmid pHcGAaPC1 ATCC 57090, 57091), hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Inducible yeast promoters have the additional advantage of transcription controlled by growth conditions. Such promoters include the promoter regions for alcohol dehydrogenase 2, isocytochrome C, acid phosphotase, degradative enzymes associated with nitrogen metabolism, metallothionein (contained on plasmid vector pCL28XhoLHBPV ATCC 39475, U.S. Pat. No. 4,840,896), glyceraldehyde 3-phosphate dehydrogenase, and enzymes responsible for maltose and galactose utilization (GAL1 found on plasmid pRY121 ATCC 37658 and on plasmid pPSR-8, described below). Suitable vectors and promoters for use in yeast expression are further described by R. Hitzeman et al., in European Patent Publication No. 73,657A. Yeast enhancers such as the UAS Gal enhancer from *Saccharomyces cerevisiae* (found in conjunction with the CYC1 promoter on plasmid YEpsec—hI1beta, ATCC 67024), also are advantageously used with yeast promoters.

A variety of expression vectors useful in the present invention are well known in the art. For expression in Saccharomyces, the plasmid YRp7, for example, (ATCC-40053, Stinchcomb, et al., 1979, *Nature* 282:39; Kingsman et al., 1979, *Gene* 7:141 ; Tschemper et al., 1980, *Gene* 10:157) is commonly used. This plasmid contains the trp gene which provides a selection marker for a mutant strain of yeast lacking the ability to grow in tryptophan, for example ATCC no. 44076 or PEP4-1 (Jones, 1977, *Genetics* 85:12).

Expression vectors useful in the expression of Afl-MDR1 can be constructed by a number of methods. For example, the cDNA sequence encoding Afl-MDR1 can be synthesized using DNA synthesis techniques such as those described above. Such synthetic DNA can be synthesized to contain cohesive ends that allow facile cloning into an appropriately digested expression vector. For example, the cDNA encoding Afl-MDR1 can be synthesized to contain NotI cohesive ends. Such a synthetic DNA fragment can be ligated into a NotI-digested expression vector such as pYES-2 (Invitrogen Corp., San Diego Calif. 92121). The resultant plasmid is designated herein as pPSR-8. Plasmid pPSR-8 is useful for the expression of the Afl-MDR1 in *Saccharomyces cerevisiae*.

Plasmid pPSR-8 can also be constructed in the following manner. Logarithmic phase *Aspergillus flavus* mycelia are disrupted by grinding under liquid nitrogen according to the procedure of Minuth et al., 1982 (Current Genetics 5:227–231). *Aspergillus flavus* mRNA is preferably isolated from the disrupted mycelia using the QuickPrep™ mRNA Purification Kit (Pharmacia Biotech) according to the instructions of the manufacturer. cDNA is produced from the isolated mRNA using the TimeSaver® cDNA Synthesis Kit (Pharmacia Biotech) using oligo (dT) according to the procedure described by the manufacturer. In this process an EcoRI/NotI adapter (Stratagene, Inc.) is ligated to each end of the double stranded cDNA. The adapter modified cDNA is ligated into the vector Lambda Zap$^R$II using the Predigested Lambda Zap$^R$II/EcoRI/CIAP Cloning Kit (Stratagene, Inc.) according to the instructions of the manufacturer to create a cDNA library.

The library is screened for full-length cDNA encoding Afl-MDR1 using a $^{32}$P-radiolabeled fragment of the Afl-MDR1 gene. This radiolabeled fragment is produced from the Afl-MDR1 genomic DNA present in plasmid pPSR-6. Utilizing the polymerase chain reaction (Gene Amp® Kit, Perkin Elmer Cetus, Norwalk, CT) and the following primers: 5'-TATCTATCGATATGCGACTCG-3' (SEQ. ID. No: 3); and 5'-GTAGACCACATTCTTGGTCAG-3' (SEQ. ID. No: 4), a Afl-MDR1 radiolabeled fragment is obtained. This radiolabeled fragment is used to probe the *Aspergillus flavus* cDNA library using standard hybridization techniques (Maniatis et al. 1992). In this manner, a full-length cDNA clone is recovered from the *Aspergillus flavus* cDNA library. A full-length cDNA clone recovered from the library is removed from the Lambda Zap$^R$II vector by digestion with the restriction endonuclease NotI which produces an approximately 4200 base pair DNA fragment encoding Afl-MDR1. The vector DNA fragment and the desired approximately 4200 base pair NotI DNA restriction fragment are separated by agarose gel electrophoresis. The desired approximately 4200 base pair NotI DNA fragment encoding Afl-MDR1 is isolated by cutting out that portion of the agarose gel containing the fragment and electroeluting the DNA using a Centrilutor™ Micro-electroeluter (Amicon, Inc.) according to the manufacturer's instructions. The isolated approximately 4200 base pair NotI restriction fragment encoding Afl-MDR1 is ligated to NotI digested pYES2 vector DNA. The correct orientation of the insert DNA is screened for by restriction endonuclease digestion using asymmetric sites located with the coding region and the flanking vector. The resultant plasmid, pPSR-8, is useful for the expression of the Afl-MDR1 in *Saccharomyces cerevisiae*.

Figure 1:
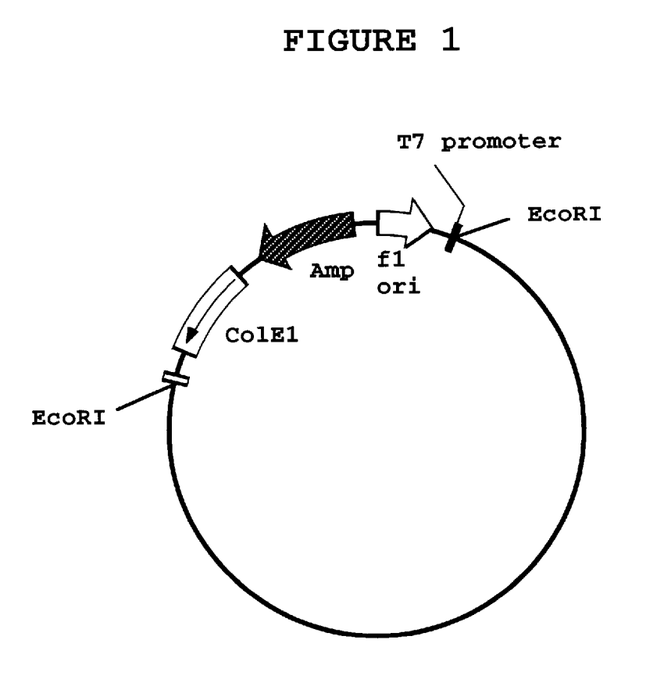
FIG. 1—A restriction enzyme site and function map of plasmid pPSR-6.
Figure 2:
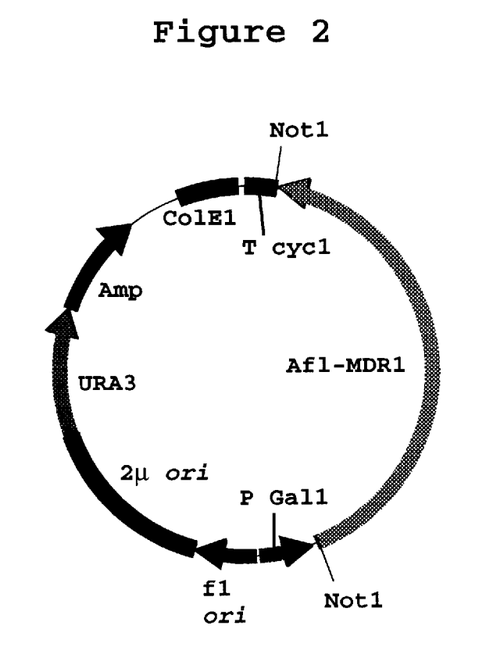
FIG. 2—A restriction enzyme site and function map of plasmid pPSR-8.

A representation of plasmid pPSR-8 is provided as FIG. 2. As noted above, this plasmid contains the Afl-MDR1 encoding DNA operably linked to the *Saccharomyces cerevisiae* GAL1 promoter (P Gal1). Plasmid pPSR-8 also comprises the yeast transcription terminator cyc1 (T cyc1) located in a position 3' to the Afl-MDR1 encoding DNA. Plasmid pPSR-8 further comprises the ColE1 origin of replication (ColE1) which allows replication in *Escherichia coli* host cells, and the ampicillin resistance gene (Amp) for selection of *E. coli* cells transformed with the plasmid grown in the presence of ampicillin. Plasmid pPSR-8 further comprises the yeast $2\mu$ origin of replication ($2\mu$ ori) allowing replication in yeast host cells, the yeast URA3 gene for selection of *S. cerevisiae* cells transformed with the plasmid grown in a medium lacking uracil, and the origin of replication from the f1 filamentous phage.

In a preferred embodiment of the invention *Saccharomyces cerevisiae* INVSc1 or INVSc2 cells (Invitrogen Corp., Sorrento Valley Blvd., San Diego Calif. 92121) are employed as host cells, but numerous other cell lines are available for this use. The transformed host cells are plated on an appropriate medium under selective pressure (minimal medium lacking uracil). The cultures are then incubated for a time and temperature appropriate to the host cell line employed.

The techniques involved in the transformation of yeast cells such as *Saccharomyces cerevisiae* cells are well known in the art and may be found in such general references as Ausubel et al., *Current Protocols in Molecular Biology* (1989), John Wiley & Sons, New York, N.Y. and supplements. The precise conditions under which the transformed yeast cells are cultured is dependent upon the nature of the yeast host cell line and the vectors employed.

Nucleic acid, either RNA or DNA, which encodes Afl-MDR1, or a portion thereof, is also useful in producing nucleic acid molecules useful in diagnostic assays for the detection of Afl-MDR1 mRNA, Afl-MDR1 cDNA, or Afl-MDR1 genomic DNA. Further, nucleic acid, either RNA or DNA, which does not encode Afl-MDR1, but which nonetheless is capable of hybridizing with Afl-MDR1 encoding DNA or RNA is also useful in such diagnostic assays. These nucleic acid molecules may be covalently labeled by known methods with a detectable moiety such as a fluorescent group, a radioactive atom or a chemiluminescent group. The labeled nucleic acid is then used in conventional hybridization assays, such as Southern or Northern hybridization assays, or polymerase chain reaction assays (PCR), to identify hybridizing DNA, cDNA, or RNA molecules. PCR assays may also be performed using unlabeled nucleic acid molecules. Such assays may be employed to identify Afl-MDR1 vectors and transformants and in in vitro diagnosis to detect Afl-MDR1-like mRNA, cDNA, or genomic DNA from other organisms.

U.S. patent application Ser. No. 08/111680, the entire contents of which are hereby incorporated herein by reference, describes the use of combination therapy involving an antifungal agent possessing a proven spectrum of activity, with a fungal MDR inhibitor to treat fungal infections. This combination therapy approach enables an extension of the spectrum of antifungal activity for a given antifungal compound which previously had only demonstrated limited clinically relevant antifungal activity. Similarly, compounds with demonstrated antifungal activity can also be potentiated by a fungal MDR inhibitor such that the antifungal activity of these compounds is extended to previously resistant species. To identify compounds useful in such combination therapy the present invention provides an assay method for identifying compounds with *Aspergillus flavus* MDR inhibition activity. Host cells that express Afl-MDR1 provide an excellent means for the identification of compounds useful as inhibitors of *Aspergillus flavus* MDR activity. Generally, the assay utilizes a culture of a yeast cell transformed with a vector which provides expression of Afl-MDR1. The expression of the Afl-MDR1 by the host cell enables the host cell to grow in the presence of an antifungal compound to which the yeast cell is sensitive to in the untransformed state. Thus, the transformed yeast cell culture is grown in the presence of i) an antifungal agent to which the untransformed yeast cell is sensitive, but to which the transformed host cell is resistant, and ii) a compound that is suspected of being an MDR inhibitor. The effect of the suspected MDR inhibitor is measured by testing for the ability of the antifungal compound to inhibit the growth of the transformed yeast cell. Such inhibition will occur if the suspected *Aspergillus flavus* MDR inhibitor blocks the ability of the Afl-MDR1 to prevent the antifungal compound from acting on the yeast cell. An illustrative example of such an assay is provided in Example 3.

In order to illustrate more fully the operation of this invention, the following examples are provided, but are not to be construed as a limitation on the scope of the invention.

EXAMPLE 1

Source of the MDR encoding Genomic DNA of *Asoercillus flavus*

Isolation of Plasmid DPSR-6

A lyophil of *Escherichia coli* XL1-Blue/pPSR-6 can be obtained from the Northern Regional Research Laboratories (NRRL), Peoria, Ill. 61604, under the accession number NRRL B-21406. Plasmid pPSR-6 may be isolated from NRRL B-21406 using techniques that are well-known to those skilled in the art. See Sambrook et al., *Molecular Cloning: A Laboratory Manual* (1988), Cold Spring Harbor Laboratory Press, Cold Spring Harbor, N.Y. or Ausubel et al., *Current Protocols in Molecular Biology* (1989), John Wiley & Sons, New York, N.Y. and supplements.

EXAMPLE 2

Expression of the Afl-MDR1 Protein

*Saccharomyces cerevisiae* INVSc1 cells (Invitrogen Corp., San Diego Calif. 92191) are transformed with the plasmid pPSR-8 by the technique described by J. D. Beggs, 1988, *Nature* 275:104–109). The transformed yeast cells are grown in a broth medium containing YNB/CSM-Ura/raf (YNB/CSM-Ura [Yeast Nitrogen Base (Difco Laboratories, Detroit, Mich.) supplemented with CSM-URA (Bio 101, Inc.)] supplemented with 4% raffinose) at 28° C. in a shaker incubator until the culture is saturated. To induce expression of the Afl-MDR1, a portion of the culture is used to inoculate a flask containing YNB/CSM-Ura medium supplemented with 2% galactose (YNB/CSM-Ura/gal) rather than raffinose as the sole carbon source. The inoculated flask is incubated at 28° C. for about 16 hours.

EXAMPLE 3

Antifungal Potentiator Assay

Approximately $1\times10^6$ cells of a *Saccharomyces cerevisiae* INVSc1/pPSR-8 culture are delivered to each of several agar plates containing YNB/CSM-Ura/gal. The agar surface is allowed to dry in a biohazard hood. *Saccharomyces cerevisiae* INVSc1/pPSR-8 cells express the Afl-MDR1 activity.

An antifungal compound that the untransformed yeast cell is typically sensitive to, such as R106I (U.S. Pat. No. 5,057,493, which is hereby incorporated herein by reference), is dissolved in 100% ethanol at a concentration of either 1 or 7 mg/ml. Twenty $\mu$l of the 1 mg/ml solution is delivered to an antibiotic susceptibility test disc (Difco Laboratories, Detroit, Mich.). After addition of the antifungal solution the disc is allowed to air dry in a biohazard hood. When dry, the disc is placed on the surface of the petri plates containing the *Saccharomyces cerevisiae* INVSc1/pPSR-8 cells.

Compounds to be tested for the ability to inhibit Afl-MDR1 are dissolved in dimethylsulfoxide (DMSO). The amount of compound added to the DMSO depends on the solubility of the individual compound to be tested. Twenty $\mu$l of the suspensions containing a compound to be tested are delivered to an antibiotic susceptibility test disc (Difco Laboratories, Detroit, Mich.). The disc is then placed on the surface of the dried petri plates containing the *Saccharomyces cerevisiae* INVSc1/pPSR-8 cells approximately 2 cm from the antifungal-containing disc. Petri plates containing the two discs are incubated at 28° C. for about 16–48 hours.

Following this incubation period, the petri plates are examined for zones of growth inhibition around the discs. A zone of growth inhibition near the antifungal disc on the test plate indicates that the compound being tested for MDR inhibition activity blocks the activity of Afl-MDR1 and allows the antifungal compound to inhibit the growth of the yeast host cell. Such compounds are said to possess MDR inhibition activity. Little or no zone of growth inhibition indicates that the test compound does not block MDR activity and, thus, the Afl-MDR1 is allowed to act upon the antifungal compound to prevent its activity upon the host cell.

We claim:

1. An isolated nucleic acid molecule that encodes a multiple drug resistance protein of *Aspergillus flavus* AFl-MDR-1.

2. A nucleic acid molecule of claim 1 which is DNA.

3. The nucleic acid molecule of claim 2 that is SEQ. ID. No. 1.

4. The nucleic acid molecule of claim 1 that is genomic DNA.

5. A nucleic acid molecule of about 21 nucleotides of Seq. ID No.: 1 which specifically hybridizes to DNA encoding a multiple drug resistance protein and which is labeled with a detectable moiety.

6. A nucleic acid molecule of claim 4 wherein the detectable moiety is selected from the group consisting of a fluorescent label, a radioactive atom, and a chemiluminescent label.

7. A vector comprising the nucleic acid of claim 1.

8. A vector comprising the nucleic acid of claim 2.

9. A vector comprising the nucleic acid of claim 3.

10. A vector comprising the nucleic acid of claim 4.

11. A host cell containing the vector of claim 7.
12. A host cell containing the vector of claim 8.
13. A host cell containing the vector of claim 9.
14. A host cell containing the vector of claim 10.
15. The host cell of claim 11 that is a yeast cell.
16. The host cell of claim 12 that is a yeast cell.
17. The host cell of claim 13 that is a yeast cell.
18. The host cell of claim 14 that is a yeast cell.
19. A method for determining the fungal MDR inhibition activity of a compound which comprises:

a) growing a culture of yeast cells, transformed with a vector which provides expression of the Afl-MDR-1, in the presence of:

(i) an antifungal agent to which said yeast cell is resistant, but to which said yeast cell is sensitive in its untransformed state;

(ii) a compound suspected of possessing *Aspergillus flavus* MDR inhibition activity; and b) determining the fungal MDR inhibition activity of said compound by measuring the ability of the antifungal agent to inhibit the growth of said yeast cell.

20. A method of claim 19 wherein the yeast cell is *Saccharomyces cerevisiae*.

\* \* \* \* \*

UNITED STATES PATENT AND TRADEMARK OFFICE
CERTIFICATE OF CORRECTION

PATENT NO.   : 5,773,214

DATED        : June 30, 1998

INVENTOR(S)  : Robert B. Peery and Paul L. Skatrud

It is certified that an error appears in the above-identified patent and that said Letters Patent is hereby corrected shown below:

Column 7, line 35, reads, "*Asoercillus flavus*"; should read, "*Aspergillus flavus*".

Signed and Sealed this

Twentieth Day of October, 1998

Attest:

BRUCE LEHMAN

*Attesting Officer*     *Commissioner of Patents and Trademarks*